US00PP12388P2

(12) United States Plant Patent
van der Knaap

(10) Patent No.: US PP12,388 P2
(45) Date of Patent: Feb. 5, 2002

(54) SPATHIPHYLLUM PLANT NAMED 'SPALIFA'

(75) Inventor: Adrianus Leonardus Joseph van der Knaap, Naaldwijk (NL)

(73) Assignee: KP Holland Selection, Naaldwijk (NL)

( * ) Notice: Subject to any disclaimer, the term of this patent is extended or adjusted under 35 U.S.C. 154(b) by 0 days.

(21) Appl. No.: 09/320,929

(22) Filed: May 27, 1999

(51) Int. Cl.[7] ..... A01H 5/00

(52) U.S. Cl. ..... Plt./364

(58) Field of Search ..... Plt./364

(56) References Cited

PUBLICATIONS

UPOV–ROM GTITM Computer Database, 2000/06, GTI Jouve Retrieval Software, citation for 'Spalifa', Feb. 1998.*

The New Royal Horticultural Society Dictionary of Gardening, vol. 4, The Stockton Press, New York, pp. 345–346, 1992.*

* cited by examiner

*Primary Examiner*—Bruce R. Campell
*Assistant Examiner*—Anne Marie Grunberg
(74) *Attorney, Agent, or Firm*—C. A. Whealy

(57) ABSTRACT

A distinct cultivar of Spathiphyllum plant named 'Spalifa', characterized by its large upright plants that are outwardly arching; large, glossy, dark green leaves that are oblong/elliptic in shape; numerous inflorescences that are positioned upright and above the foliage on strong and erect scapes; large white spathes; year-round continuous flowering; and good post-production longevity.

1 Drawing Sheet

BACKGROUND OF THE INVENTION

The present invention relates to a new and distinct cultivar of Spathiphyllum plant, botanically known as *Spathiphyllum schott.*, and hereinafter referred to by the cultivar name Spalifa.

The new Spathiphyllum is a product of a planned breeding program conducted by the Inventor in Naaldwijk, The Netherlands. The objective of the program is to create new Spathiphyllum cultivars that are large with large dark green leaves, large white spathes, continuous year-round flowering, and good post-production longevity.

The new Spathiphyllum originated from a cross by the Inventor in March, 1993 of the Inventor's proprietary *Spathiphyllum Schott.* selection code number 156 as the female, or seed, parent with the Inventor's proprietary *Spathiphyllum Schott.* selection code number 701 as the male, or pollen, parent. The cultivar Spalifa was discovered and selected by the Inventor as a plant within the progeny of the stated cross in a controlled environment in Naaldwijk, The Netherlands in January, 1995.

Asexual propagation of the new cultivar by tissue culture in Maasdijk, The Netherlands, has shown that the unique features of this new Spathiphyllum plant are stable and reproduced true to type in successive generations of asexual propagation.

BRIEF SUMMARY OF THE INVENTION

The new Spathiphyllum has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Spalifa. These characteristics in combination distinguish 'Spalifa' as a new and distinct cultivar:

1. Large upright plants that are outwardly arching.
2. Large, glossy, dark green leaves that are oblong/elliptic in shape.
3. Numerous inflorescences that are positioned upright and above the foliage on strong and erect scapes.
4. Large white spathes.
5. Year-round continuous flowering.
6. Good post-production longevity.

The new Spathiphyllum can be compared to the female parent, the Inventor's proprietary selection code number 156. In side-by-side comparisons conducted by the Inventor in Naaldwijk, The Netherlands, plants of the new Spathiphyllum have larger leaves, darker green leaves, and larger spathes than plants of the selection code number 156.

The new Spathiphyllum can be compared to the male parent, the Inventor's proprietary selection code number 701. In side-by-side comparisons conducted by the Inventor in Naaldwijk, The Netherlands, plants of the new Spathiphyllum have darker leaves, larger spathes, and thicker petioles and peduncles than plants of the selection code number 708.

The new Spathiphyllum can be compared to the Spathiphyllum cultivar Sensation, not patented. In side-by-side comparisons conducted by the Inventor in Naaldwijk, The Netherlands, plants of the new Spathiphyllum differ from plants of the cultivar Sensation in the following characteristics:

1. Plants of the new Spathiphyllum are more freely clumping and have more shoots than plants of the cultivar Sensation.
2. Plants of the new Spathiphyllum have much darker green leaves than plants of the cultivar Sensation.
3. Plants of the new Spathiphyllum have more inflorescences than plants of the cultivar Sensation.

BRIEF DESCRIPTION OF THE PHOTOGRAPH

The accompanying colored photograph illustrates the overall appearance of the new Spathiphyllum, showing the colors as true as it is reasonably possible to obtain in colored reproductions of this type. The photograph comprises a side perspective view of a typical potted plant of the cultivar Spalifa. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe two-year old plants grown in 42-cm containers in Naaldwijk, The Netherlands, in a glass greenhouse with an average day and night temperature of 21° C. with a light level of about 200 W/m$^2$.

Botanical classification: *Spathiphyllum schott.* cultivar Spalifa.

Parentage:

*Female parent.*—Inventor's proprietary *Spathiphyllum schott.* selection code number 156.

*Male parent.*—Inventor's proprietary *Spathiphyllum schott.* selection code number 701.

Propagation:

*Method.*—By tissue culture.

*Time to initiate roots on a tissue-cultured plant.*—About 11 to 14 days at 21° C.

*Rooting habit.*—Numerous fleshy roots.

Plant description:

*Plant shape.*—Upright, outwardly spreading inverted triangle, symmetrical.

*Growth habit.*—Erect when young, becoming outwardly arching as leaves develop. Freely clumping, bushy and dense; about eight shoots per plant. Appropriate for 19-cm and larger containers.

*Plant height.*—About 100 cm from soil level to apex of leaf plane and about 115 cm from soil level to apex of spathes.

*Plant width.*—About 150 cm.

*Growth rate.*—Moderate.

*Crop time.*—About 50 and 60 weeks are usually required from planting of young plants to finished plants in 21 and 26-cm containers, respectively.

*Foliage description.*—Quantity: Usually about 55 leaves per clump. Length: About 45 to 50 cm. Width: About 20 to 25 cm. Shape: Obling/elliptic. Apex: Apiculate, cirrhous. Base: Obtuse. Margin: Entire; slightly undulated. Texture: Smooth, glabrous, glossy, slightly undulate; rugose. Color: Young leaves, upper surface: Darker than 141A. Young leaves, lower surface: Close to 138B to 138C. Mature leaves, upper surface: Close to 136A to 139A. Mature leaves, lower surface: Close to 137B to 138B. Venation, upper surface: 136A to 139A. Venation, lower surface: Close to 143A. Petiole: Length: About 50 to 60 cm. Width: About 1 cm. Geniculum length: About 3 to 6 cm. Geniculum diameter: About 8 to 10 mm. Color: Close to 137A to 139A; geniculum, close to 138B.

Inflorescence description:

*Inflorescence arrangement.*—Spathe with spadix held above the foliage. Flowering structures arise from leaf axils. Freely flowering; continuous flowering year-round; numerous spathes/spadices per plant.

*Inflorescence longevity.*—Spathes/spadices last about six weeks under interior conditions; persistent; slightly fragrant.

*Flowers.*—Quantity of flowers per spadix: Numerous, about 150 to 200 flowers. Shape: Conical. Diameter: About 2 to 3 mm.

*Spathe.*—Length: About 21 to 27 cm. Width: About 14 to 17 cm. Shape: Lanceolate/elliptic. Apex: Apiculate, cirrhous, undulating. Base: Obtuse to rounded. Margin: Entire. Aspect: Upright, erect. Texture: Glabrous, satiny, slightly blistering. Color: When opening: 155D to 159D. Front surface: 155D to 159D; veins, 155C. Back surface: 155C to 155D; veins, 143C. After senescence: 141C.

*Spadix.*—Length: About 8 to 11 cm. Diameter: About 1.8 to 2 cm. Shape: Columnar. Cross section: Rounded. Longitudinal axis: Straight, erect. Color: 159C to 158C.

*Scape.*—Length: About 70 to 90 cm. Aspect: Strong and erect. Color: 137A to 139A.

*Reproductive organs.*—Androecium: Anthers: Four per flower. Pollen color: Creamy white, 159C. Gynoecium: Pistils: Four per flower. Stigma shape: Rounded. Stigma color: 159B.

Disease resistance: Plants of the new Spathiphyllum have not been shown to be resistant to diseases common to Spathiphyllum.

Seed development: Seed development on plants of the new Spathiphyllum has not been observed.

It is claimed:

1. A new and distinct cultivar of Spathiphyllum plant named 'Spalifa', as illustrated and described.

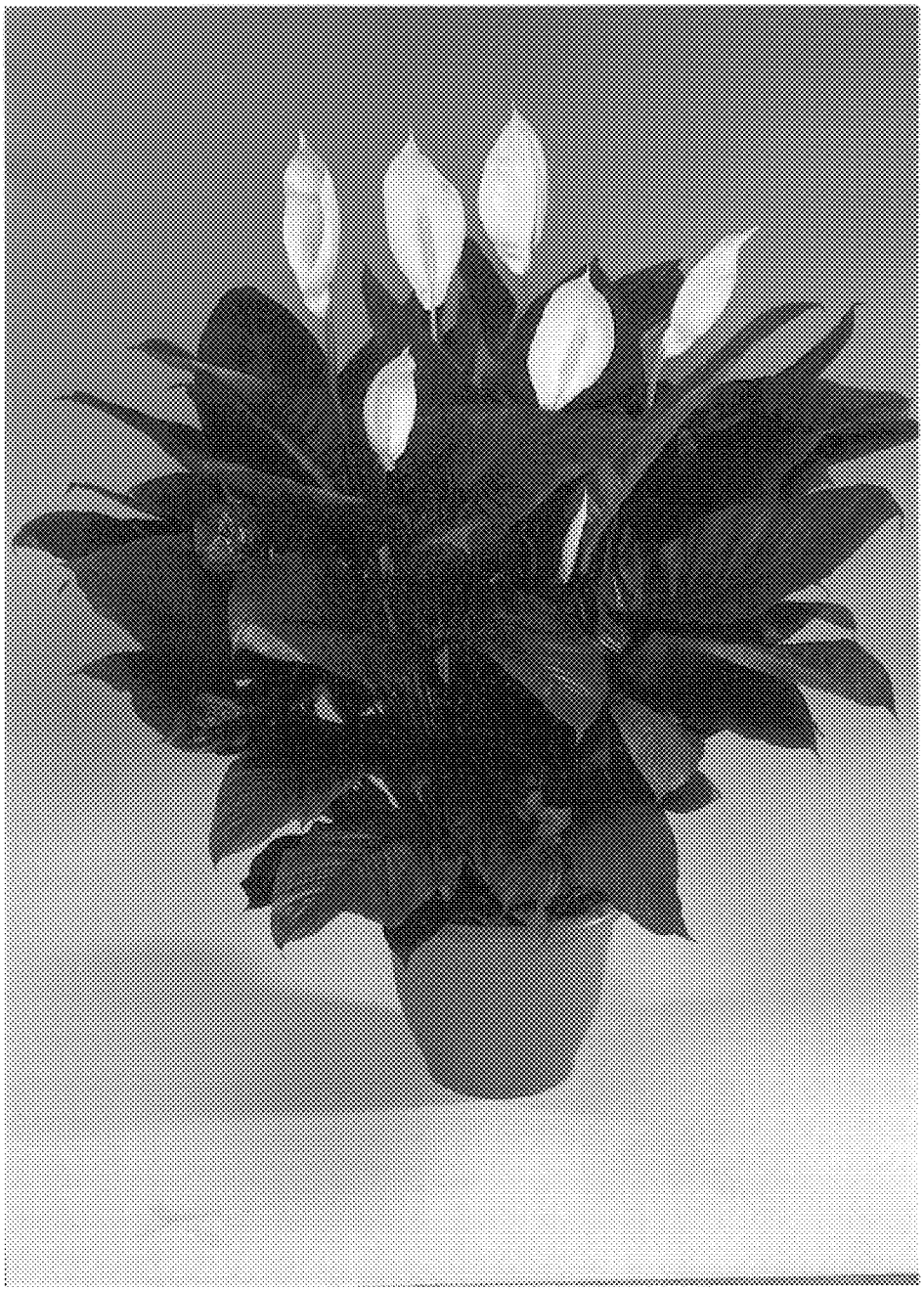

* * * * *